(12) United States Patent
Hirayama et al.

(10) Patent No.: US 10,342,989 B2
(45) Date of Patent: Jul. 9, 2019

(54) MAGNETIC FLUX IRRADIATION DEVICES AND COMPONENTS

(71) Applicants: Dai-Ichi High Frequency Co., Ltd., Tokyo (JP); Nanotherapy Co., Ltd., Tokyo (JP)

(72) Inventors: Kotaro Hirayama, Tokyo (JP); Shuichiro Miyata, Tokyo (JP)

(73) Assignee: DAI-ICHI HIGH FREQUENCY CO., LTD., Chuo-Ku (JP)

( * ) Notice: Subject to any disclaimer, the term of this patent is extended or adjusted under 35 U.S.C. 154(b) by 383 days.

(21) Appl. No.: 15/022,459

(22) PCT Filed: Sep. 22, 2014

(86) PCT No.: PCT/JP2014/075767
§ 371 (c)(1),
(2) Date: Mar. 16, 2016

(87) PCT Pub. No.: WO2015/041374
PCT Pub. Date: Mar. 26, 2015

(65) Prior Publication Data
US 2016/0317829 A1    Nov. 3, 2016

(30) Foreign Application Priority Data
Sep. 20, 2013  (JP) ................. 2013-196117

(51) Int. Cl.
*A61N 2/02* (2006.01)
*A61N 2/00* (2006.01)
*H01F 7/20* (2006.01)

(52) U.S. Cl.
CPC .............. *A61N 2/02* (2013.01); *A61N 2/004* (2013.01); *H01F 7/20* (2013.01); *H01F 7/202* (2013.01)

(58) Field of Classification Search
CPC .............................................. A61N 2/00–2/12
See application file for complete search history.

(56) References Cited

U.S. PATENT DOCUMENTS

| | | |
|---|---|---|
| 6,520,903 B1 | 2/2003 | Yamashiro |
| 7,282,479 B2 | 10/2007 | Ito et al. |
| 7,670,676 B2 | 3/2010 | Horiishi et al. |
| 8,214,053 B2 | 7/2012 | Hirayama et al. |
| 2008/0089472 A1 | 4/2008 | Yoon |
| 2009/0319010 A1 | 12/2009 | Hirayama et al. |
| 2011/0165255 A1 | 7/2011 | Kobayashi et al. |

(Continued)

FOREIGN PATENT DOCUMENTS

| | | |
|---|---|---|
| CN | 1846808 | 10/2006 |
| DE | 10332771 | 3/2005 |

(Continued)

OTHER PUBLICATIONS

International Application No. PCT/JP2014/075767, International Search Report and Written Opinion, dated Dec. 16, 2014.

*Primary Examiner* — Thaddeus B Cox
(74) *Attorney, Agent, or Firm* — Kilpatrick Townsend and Stockton LLP (57) ABSTRACT

Magnetic flux irradiation devices having a cylindrical coil and a magnetic core including an optical transmission path are provided. Magnetic cores are also provided. Methods and systems for using such devices are also provided. The optical transmission path is configured to transmit light incident on an irradiation target, or thermal radiation emitted from the irradiation target.

19 Claims, 6 Drawing Sheets

(56) References Cited

U.S. PATENT DOCUMENTS

2012/0016174 A1  1/2012  De Taboada et al.
2015/0119961 A1  4/2015  Kobayashi et al.

FOREIGN PATENT DOCUMENTS

| | | |
|---|---|---|
| EP | 1036574 | 9/2000 |
| JP | 4734006 | 4/2001 |
| JP | 3737054 | 11/2005 |
| JP | 3767820 | 2/2006 |
| JP | 3783811 | 3/2006 |
| JP | 4097580 | 3/2008 |
| JP | 4255466 | 2/2009 |
| JP | 4338961 | 7/2009 |
| JP | 4731185 | 4/2011 |
| JP | 4966575 | 4/2012 |
| JP | 5031979 | 7/2012 |
| JP | 5321772 | 7/2013 |
| WO | WO 1998/06342 | 2/1998 |
| WO | WO 2005/089869 | 9/2005 |
| WO | WO 2011/089472 | 7/2011 |

MAGNETIC FLUX IRRADIATION DEVICES AND COMPONENTS

CROSS-REFERENCE TO RELATED APPLICATIONS

The present application is a § 371 national stage application of International Application No. PCT/JP2014/075767, filed Sep. 22, 2014, which claims the benefit of priority to Japanese Application No. 2013-196117, filed Sep. 20, 2013. Each of these applications are hereby incorporated by reference in their entireties herein.

TECHNICAL FIELD

This disclosure relates to magnetic flux irradiation devices having a magnetic core positioned within a coil that are configured to irradiate magnetic flux from one end of the coil when electrical current is supplied to the coil.

BACKGROUND

Currently, in a local thermotherapy, such as a hyperthermia therapy method, a magnetic flux irradiation device is used to locally heat an affected part. Specifically, the magnetic flux irradiation device has a cylindrical coil, and a magnetic core that is inserted into the coil to be parallel to an axis of the coil When alternating current is supplied to the coil when one end of the magnetic core is disposed to face the affected part, an alternating magnetic flux is irradiated to the affected part from the one end of the magnetic core. Magneto-sensitive heating element particulates that are provided in the affected part generate heat, and the affected part is heated to effect the therapy.

In such a magnetic flux irradiation device, a density of the magnetic flux axially emitted from one end of the magnetic core is significantly attenuated as it goes away from the axis of the coil. Therefore, in order to effectively irradiate the magnetic flux emitted from one end of the magnetic core to the affected part, it is necessary to accurately position the coil with respect to the affected part. However, in conventional magnetic flux irradiation devices, it is not easy to accurately grasp the axis position of the coil from the outside, and it is difficult to accurately position the coil with respect to the affected part.

In addition, during irradiation of the magnetic flux with respect to the affected part, because the conventional magnetic flux irradiation device is disposed to be sufficiently close to the affected part, the thermal radiation emitted from the affected part is blocked by the device. Therefore, it is not possible to measure the temperature of the affected part by using the thermal radiation emitted from the affected part.

SUMMARY

The present disclosure provides magnetic flux irradiation devices. In some aspects, the magnetic flux irradiation devices include a cylindrical coil, and a magnetic core disposed within the cylindrical coil and parallel to an axis of the cylindrical coil, the magnetic core having an optical transmission path formed therein and traversing from a first end of the magnetic core to a second end of the magnetic core. In some aspects, the magnetic flux irradiation device is configured to irradiate magnetic flux from the first end of the magnetic core responsive to electric current supplied to the cylindrical coil. In some aspects, the optical transmission path is configured to transmit light incident on a irradiation target positioned to face the first end of the magnetic core, or thermal radiation emitted from the irradiation target positioned to face the first end of the magnetic core, or both.

In another aspect, this disclosure provides a system comprising a magnetic flux irradiation device as described above, a power supply configured to supply electrical current to the cylindrical coil of the magnetic flux irradiation device, and a computer configured to control operation of the magnetic flux irradiation device, or process data obtained from monitoring an irradiation target upon which the magnetic flux irradiation device is used, or both.

In another aspect, this disclosure provides methods of irradiating an irradiation target site with magnetic flux irradiation, the method comprising providing a magnetic flux irradiation device as described above; positioning an irradiation target to face the first end of the magnetic core using the optical transmission pathway to determine the position of irradiation target; and irradiating the irradiation target site with magnetic flux irradiation by supplying electrical current to the cylindrical coil to generate magnetic flux on the magnetic core that is emitted from the first end of the magnetic core to the irradiation target.

In one aspect, this disclosure provides magnetic flux irradiating devices that are configured to receive a magnetic core as descibed above.

In another aspect, this disclosure provides magnetic cores having an optical transmission path formed therein and traversing from a first end of the magnetic core to a second end of the magnetic core as described above.

An object achieved by the magnetic flux irradiation devices is accurate and easy positioning of the device with respect to an irradiation target.

DETAILED DESCRIPTION

Certain embodiments and features of the present disclosure relate to magnetic flux irradiating devices having an optical transmission pathway. Certain embodiments and features relate to systems including such magnetic devices. Certain embodiments and features relate to methods of irradiating an irradiation target using such devices. Certain embodiments and features relate to magnetic flux irradiation devices that are configured to receive a magnetic core having an optical transmission pathway. Certain embodiments and features relate to magnetic core having an optical transmission pathway.

For example, a magnetic flux irradiating device according to one aspect is made to include a cylindrical coil and a magnetic core. The magnetic core is positioned within the cylindrical coil to be parallel to an axis of the cylindrical coil. An optical transmission path is formed in the magnetic core that allows light or thermal radiation to pass from one of the magnetic core to the other. When an electrical current is supplied to the core, magnetic flux is generated on the magnetic core and emitted from one end. When an irradiation target is positioned facing the one end of the magnetic core, it is irradiated with the magnetic flux.

The magnetic flux irradiating device may also include a laser component, such as a laser. The optical transmission path inside the cylindrical coil permits transmission of light (for example, a laser beam) from one end of the magnetic core to the other towards the end that can be positioned to face an irradiation target. This may allow the user to visually assess the irradiation target via the optical transmission path and thereby permit accurate and easy positioning of the device with respect to the irradiation target. The magnetic flux irradiating device may also include a thermometer, such as a radiation thermometer. The optical transmission pathway can also be used to transmit thermal radiation emitted from the irradiation target from one end of the magnetic core to the other and thereby allow measurement of the temperature of the irradiation target while it is being irradiated with the magnetic flux. The magnetic flux irradiating devices described in this disclosure can be used for localized thermotherapy, such a hyperthermia.

Magnetic cores having various configurations are contemplated as long as an optical transmission path is formed in the magnetic core that allows light or thermal radiation to pass from one of the magnetic core to the other. The dimensions (size) of the magnetic cores may be selected based on the desired frequency and use for the device. For example, the length of the core may be the same length as, or may have a shorter length than, or may have a longer length than, the coil or the coil housing. In some instances, the length of the magnetic core is about the same as the length of the coil. In one aspect, the diameter of the core may be selected to fit within the diameter of a central cavity defined within the coil and, in particular, a central cavity defined within the coil housing that houses the coil.

The magnetic core may have a uniform cross-section or may have a large cross-sectional columnar portion adjacent to a small cross-sectional columnar portion. Where the magnetic core has a large cross-sectional columnar portion adjacent to a small cross-sectional columnar portion, the ratio of the diameter of the columnar portion of the small cross-sectional area to the diameter of the columnar portion of the large cross-sectional area may be about 1:2 to about 1:3. For example, the diameter of the small columnar portion may be about 2.5 smaller than the large columnar portion. Where the magnetic core has a plurality of columnar magnetic core elements, the dimensions of the columnar magnetic core elements may be selected to fit within the diameter of a central cavity defined within the coil and, in particular, within a central cavity defined within the coil housing.

The illustrative example described above has been provided to introduce the subject matter of this disclosure and is not intended to limit the scope of the disclosure. Hereinafter, some examples will be described in detail below with reference to the accompanying drawings but other examples are within the scope of this disclosure. Additional embodiments and features are also described throughout this disclosure. The same reference indicators will be used throughout the drawings and the following description to refer to the same or like items.

Figure 1:
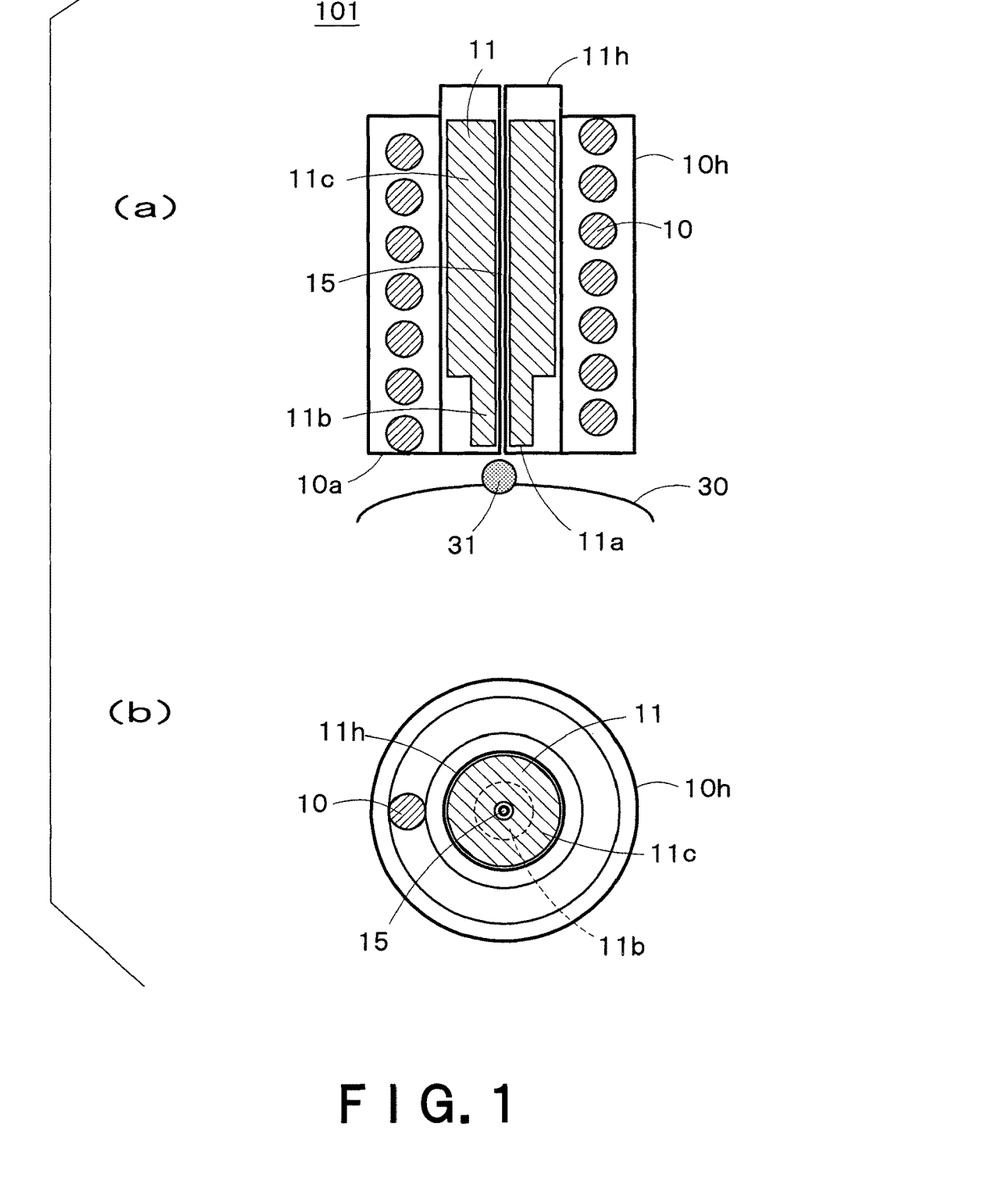
FIG. 1(a) is a schematic side cross-sectional view illustrating a magnetic flux irradiation device according to a first example.
FIG. 1(b) is a schematic top cross-sectional view illustrating the magnetic flux irradiation device of FIG. 1(a).

A magnetic flux irradiation device according to one example is shown in FIG. 1a and FIG. 1b. FIG. 1(a) is a schematic side cross-sectional view illustrating a magnetic flux irradiation device according to a first example. FIG. 1(b) is a schematic top cross-sectional view illustrating the magnetic flux irradiation device of FIG. 1(a).

As illustrated in FIGS. 1(a) and 1(b), a magnetic flux irradiation device 101 according to one aspect has a cylindrical coil 10 and a magnetic core 11 inserted into the coil 10, where the magnetic core 10 is positioned parallel to the axis of the coil 10.

In one aspect, as illustrated in FIG. 1(a), the coil 10 may be a cylindrical solenoid coil. Alternatively, in other examples, the columnar portion 11b of the small cross-sectional area and the columnar portion 11c of the large cross-sectional area may have a prismatic shape. The size of the coil 10 may be selected based on various factors, including the desired magnetic flux density, the frequency (power) to be provided to the coil, and the maximum temperature that can be dissipated. For example, based on the desired characteristics of the coil 10 and the device 101, the diameter of the coil 10 may be about 35 mm to about 140 mm. In another aspect, based on the desired characteristics of the coil 10 and the device 101, the length of the coil 10 can be about 60 mm to about 240 mm. In one example, the diameter of the coil 10 can be about 70 mm, and the axial length of the coil 10 can be about 120 mm. In another example, the diameter of the coil 10 can be about 35 mm, and the axial length of the coil 10 can be about 60 mm. In another example, the diameter of the coil 10 can be about 140 mm, and the axial length of the coil 10 can be about 240 mm. In some examples, the length of the coil is about 1.5 to about 2.0 times greater than the diameter of the coil. For example, the ratio of the length to the diameter of the coil may be about 1.65, about 1.71, about 1.88, or some other ratio between about 1.5 to about 2.0. In one example, the ratio of the length to the diameter of the coil 10 is about 1.71.

In one aspect, the dimensions (size) of the magnetic core 11 may be selected based on the desired frequency and use for the device 101. For example, the length of the core 11 may be the same length as, or may have a shorter length than, or may have a longer length than, the coil 10 or the coil housing 10h. In one aspect, the diameter of the core 11 may be selected to fit within the diameter of a central cavity defined within the coil 10 and, in particular, a central cavity defined within the coil housing 10h that houses the coil 10.

Figure 5:
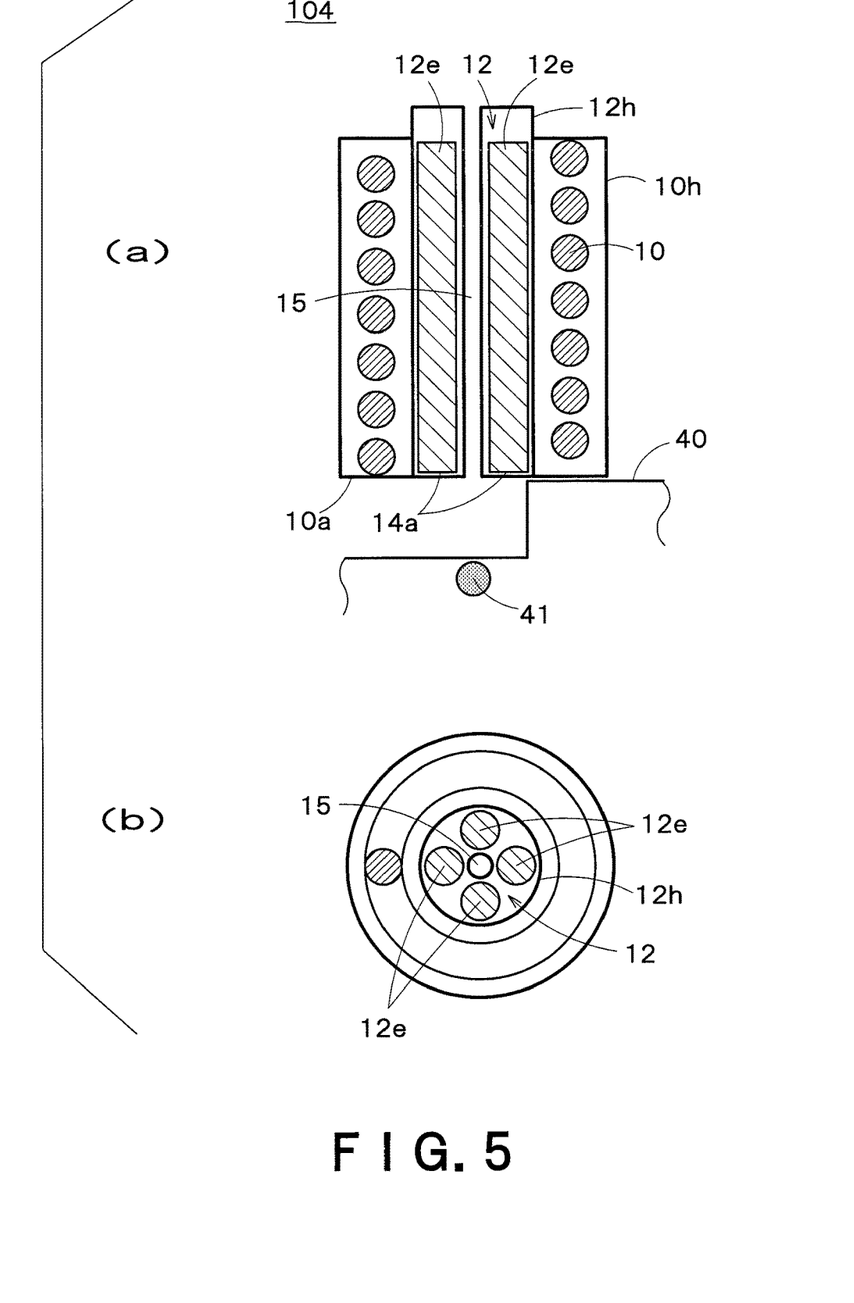
FIG. 5(a) is a schematic side cross-sectional view illustrating a magnetic flux irradiation device according to a fourth example.
FIG. 5(b) is a schematic top cross-sectional view illustrating the magnetic flux irradiation device of FIG. 5(a).

In another aspect, the magnetic core 11 may have various configurations. For example, as illustrated in FIG. 1(a), the magnetic core 11 may include a large cross-sectional columnar portion 11c adjacent to a small cross-sectional columnar portion 11b that defines the first end 11a of the magnetic core 11, and the optical transmission path 15 may be configured to pass through the columnar portion of the small cross-sectional area 11b and the columnar portion of the large cross-sectional area 11c. In this first example, the magnetic core 11 has a columnar portion 11b of a small cross-sectional area that defines a first end 11a of the magnetic core 11, and a columnar portion 11c of a large cross-sectional area adjacent to the columnar portion 11b of the small cross-sectional area that defines a second end of the magnetic core 11. In some cases, the large cross-sectional columnar portion 11c and the small cross-sectional columnar portion 11b of the magnetic core 11 are a single magnetic core component. In some cases, the large cross-sectional columnar portion 11c and the small cross-sectional columnar portion 11b of the magnetic core 11 are two adjoined magnetic core components. However, the magnetic core may have other configurations, such as illustrated, for example, in FIGS. 5 and 7.

In another aspect, the magnetic core 11 may have various shapes. In one example, as shown in FIG. 1a, the magnetic coil 11 can have a cylindrical shape. In other examples, the magnetic coil 11 can have a prismatic shape. In some examples, where the coil 11 comprises a large cross-sectional columnar portion 11c adjacent to a small cross-sectional columnar portion 11b, the columnar portion 11b and the columnar portion 11c may be cylindrical or prismatic.

For example, where the device 101 has a coil having a diameter of 70 mm and a length of 120 mm, the columnar portion 11b of the small cross-sectional area may have a diameter of 20 mm and an axial length of 20 mm, and the columnar portion 11c of the large cross-sectional area may have a diameter of 50 mm and an axial length of 100 mm. In some cases, the columnar portion 11b of the small cross-sectional area may be a cylindrical shape having a diameter of 20 mm and an axial length of 20 mm, and the columnar portion 11c of the large cross-sectional area has a cylindrical shape having a diameter of 50 mm and an axial length of 100 mm. In one aspect, the ratio of the diameter of the columnar portion 11b of the small cross-sectional area to the diameter of the columnar portion 11c of the large cross-sectional area may be about 1:2 to 1:3. For example, the diameter of the columnar portion 11b may be about may be about 2.5 smaller than the columnar portion 11c.

In one aspect, the magnetic core 11 comprises a magnetic material that restricts and channels magnetic eddy current fields. For example, in one aspect, the material of the magnetic core 11 can include a Mn—Zn ferrite material, a Ni—Zn material, an iron powder, a high flux powder, a permalloy powder, or an amorphous alloy. In one example, the material of the magnetic core 11 is a Mn—Zn ferrite material. Other magnetic materials are also contemplated for use in making the magnetic core 11.

In some instances, the material of the magnetic core 11 may be selected based on the desired frequency range for the device 101. For example, a Mn—Zn ferrite material may be selected for a desired frequency of 10 kHz to 2 MHz. In another example, a Ni—Zn material may be selected for a desired frequency range of 200 kHz to 100 Mhz. In another example, an iron powder may be selected for a desired frequency range of 100 kHz to 100 MHz. In another example, a high flux powder or a permalloy powder may be selected for a desired frequency range of 10 kHz to 1 Mhz. In another example, an amorphous alloy may be selected for a desired frequency range of 500 Hz to 250 kHz.

In one example, as illustrated in FIG. 1(a), the coil 10 is coaxially housed within a coil housing 10h having a cavity on an inner peripheral side thereof. In another aspect, the magnetic core 11 may be coaxially housed within a magnetic core housing 11h that is positioned within the cavity of the coil housing 10h. In another aspect, the magnetic core 11 is not housed within a magnetic core housing (not shown) and is instead configured to fit within the coil 10 directly.

In one aspect, the position of the first end 11a of the magnetic core 11 relative to the first end 10a of the coil 10 may vary based on the desired magnetic flux and configuration of the device 101. For example, the first end 11a of the magnetic core 11 may be positioned on the same plan as the first end 10a of the coil 10, or may protrude axially outward from the first end 10a of the coil 10, or may recede axially from the first end 10a of the coil 10.

In one example, the first end 11a of the magnetic core 11 is adapted to be positioned on the same plane as the first end 10a of the coil 10. In this disclosure, "the same plane as the first end 10a of the coil 10" includes a plane that is located on the inside of the coil 10 in the axial direction within 1 mm to 5 mm from the first end 10a of the coil 10. In other aspects, as discussed in other examples described herein, the first end 11a of the magnetic core 11 is adapted to be positioned on a different plane than the first end 10a of the coil 10.

In one aspect, a power source (not illustrated) may be electrically connected to the coil 10. In one aspect, alternating current may be supplied to the coil 10 from the power source at a predetermined frequency (for example, 50 kHz to 400 kHz), alternating magnetic flux parallel to the axial direction is formed in the magnetic core 11 inserted into the coil 10. In one aspect, the alternating magnetic flux is focused at the columnar portion 11b of the small cross-sectional area and emits from the first end 11a. In one aspect, alternating magnetic flux emitted from the first end 11a of the magnetic core 11 may irradiate an irradiation target 31 that is disposed to face the first end 11a.

In another aspect, as illustrated in FIGS. 1(a) and 1(b), an optical transmission path 15 may be formed on the inside of the coil 10. In one aspect, the optical transmission path 15 can transmit light incident on the irradiation target 31 or thermal radiation emitted from the irradiation target 31. In context of this disclosure, "transmission" includes not only passing through a material, but also passing through the air. In one aspect, the optical transmission path 15 can be formed on the axis of the coil 10. In one aspect, the optical transmission path may be formed at the coil center. In another aspect, the optical transmission path may be formed parallel to the axis of the coil.

In one example, the optical transmission path 15 is formed continuously through the columnar portion 11b of the small cross-sectional area and the columnar portion 11c of the large cross-sectional area on the axis of the coil 10 from the first end 11a to the second end of the magnetic core 11. The diameter of the optical transmission path 15 may be about 2 mm to about 50 mm. As the diameter of the magnetic core 11 increases, so may the diameter of the optical transmission path 15. For example, the diameter of the optical transmission path 15 may be about 2 mm, about 5 mm, about 8 mm, about 10 mm, about 15 mm, about 25 mm, about 35 mm, or about 50 mm, or any other diameter within about 2 mm to about 50 mm. In one example, the diameter of the optical transmission path 15 is about 5 mm. In some cases, the diameter of the optical transmission path 15 is sufficient to provide a path through the magnetic core 11 axially from one end to the other through which light (such as visible light or a laser beam) or thermal radiation can pass. However, the diameter of the optical transmission path is not so large as to impair the desired magnetic flux generated on the magnetic core 11 (regardless of the configuration of the magnetic core 11). In some examples, an opening is formed in the magnetic core housing 11h at a position corresponding axially to the optical transmission path 15 at the second end of the magnetic core 11 as illustrated in FIGS. 1a and 1b.

In one aspect, the magnetic flux density emitted from the magnetic core 11 of the device 101 is based on one or more of the size of the coil 10, the size of the magnetic core 11, the configuration of the magnetic core 11, and the frequency of the power supplied to the coil 10. Different irradiation patterns may be emitted from the magnetic flux irradiation device basedo the configuration of the replaceable magnetic core inserted within the coil. An irradiation pattern may include at least a magnetic flux density or an extent of diffusion (attenuation). For example, depending on the configuration of the magnetic core, the magnetic flux density emitted from the magnetic core may be about 0.5 mT to about 30 mT, or about 5 mT to about 20 mT, or about 10 mT to about 30 mT, or about 8 mT to about 25 mT. For example, the magnetic flux density may be about 10 mT, about 12 mT, about 15 mT, about 18 mT, about 20 mT, about 23 mT, about 25 mT, about 28 mT, or about 30 mT. For example, where the size of the coil 10 and the magnetic core 11 are small, the magnetic flux density may range from about 0.5 mT to about 15 mT. In another example, where the size of the coil 10 and the magnetic core 11 are larger, the magnetic flux density may range from about 10 mT to about 30 mT.

Figure 2:
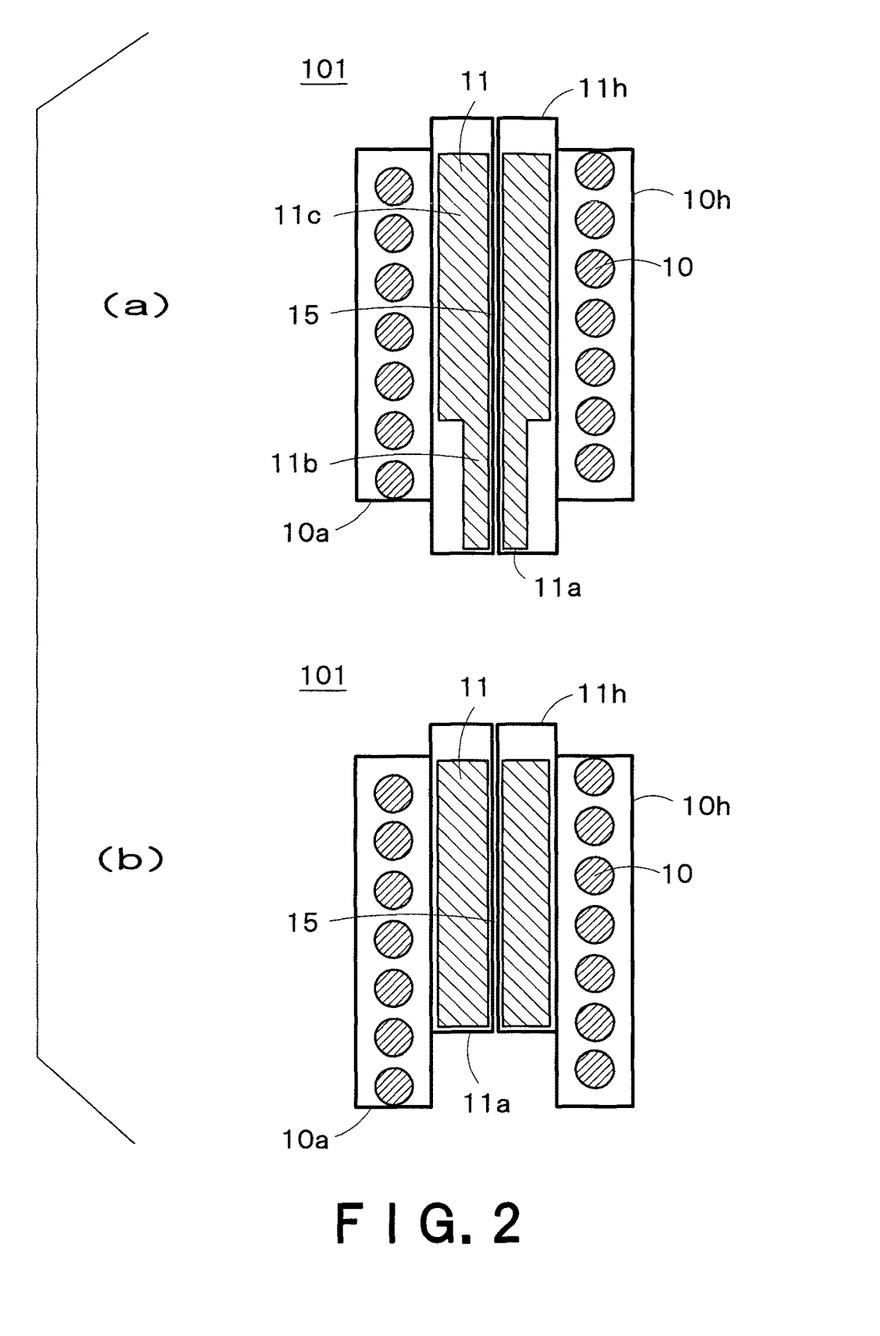
FIG. 2(a) is a schematic side cross-sectional view illustrating a modified example of the magnetic flux irradiation device of FIG. 1(a).
FIG. 2(b) is a schematic side cross-sectional view illustrating a modified example of the magnetic flux irradiation device of FIG. 1(a).

In one example, as illustrated in FIGS. 1(a) and 1(b), the first end 11a of the magnetic core 11 may be located on the same plane as the first end 10a of the coil 10. However, as discussed above, the position of the first end 11a of the magnetic core 11 relative to the first end 10a of the coil 10 is not limited to this configuration. For example, as illustrated in FIG. 2(a), the columnar portion 11b of the small cross-sectional area of the magnetic core 11 may be configured to protrude axially outward from the first end of the coil 10. In this case, the magnetic flux formed inside the magnetic core 11 can be emitted in the axial direction from the first end 11a, after being being parallel to the axial direction over a long distance by which the columnar portion 11b of the small cross-sectional area protrudes with respect to the first end 10a of the coil 10. Therefore, a diffusion start position of the magnetic flux emitted from the first end of the magnetic core 11 can be extended below (outwards from) the plane of the first end of the coil 10. In another example, as illustrated in FIG. 2(b), the columnar portion 11b of the small cross-sectional area of the magnetic core 11 may be configured to recess axially inward from the first end of the coil 10. In this instance, the magnetic flux formed inside the magnetic core 11 is emitted in the axial direction from the first end 11a into the recess formed within the coil 10 between the first end 11a of the magnetic core 11a and the first end of the magnetic coil 10a and is of large magnetic flux density (such as, for example, about 0.5 mT to about 30 mT). In one example, the magnetic flux density is about 10 mT. For example, where the columnar portion 11b of the small cross-sectional area is be a cylindrical shape having a diameter of 20 mm and an axial length of 20 mm, and the columnar portion 11c of the large cross-sectional area has a cylindrical shape having a diameter of 50 mm and an axial length of 100 mm, the magnetic flux density may be about 10 mT.

Next, the operation of the example device 101 as shown in FIG. 1(a) and FIG. 1(b) and described above will be described as an example of a case where the irradiation target 31 is located on the outer surface an irradiation object 30 having a convex shape and is irradiated with the magnetic flux.

In one aspect, the first end 11a of the magnetic core 11 is disposed to face the surface of the irradiation object 30. Upon positioning of the first end 11a of the magnetic core 11 to face the surface of the irradiation object 30, visible light emitted from the surface of the irradiation object 30 may be transmitted through the optical transmission path 15 and be emitted to the outside from the other side of the optical transmission path 15 (a side opposite to the surface of the irradiation object 30) at the second end of the magnetic core 11. Therefore, in one aspect, the surface of the irradiation object 30 may be visually checked from the other side magnetic core 11 (at the second end of the magnetic core 11) via the optical transmission path 15.

In one aspect, while the surface of the irradiation object 30 may be visually checked via the optical transmission path 15, the magnetic flux irradiation device 101 and the irradiation object 30 may be relatively moved until it is determined, by visual checking via the optical transmission path 15, that the irradiation target 31 and the device 101 are positioned as desired, such that the irradiation target 31 is aligned with the axis of the coil 10. Thus, in some aspects, the irradiation target 31 can be accurately positioned on the axis of the coil 10 adjacent to the first end 11a of the magnetic core 11. In some instances, at the position of the surface of the irradiation object 30 corresponding to the irradiation target 31, an alignment mark (not illustrated) may be denoted in advance.

In one aspect, the first end 11a of the magnetic core 11 is positioned to be sufficiently close to the irradiation target 31 to permit effective irradiation of the irradiation target 31, for example, while the irradiation target 31 is being viewed through the optical transmission path 15. For example, the first end 11a can be positioned within 5 mm to 15 cm of the irradiation target 31 depending on the intensity of the magnetic flux density emitted from the magnetic core 11. For example, the first end 11a may be positioned at a distance of about 5 mm, 10 mm, 20 mm, 30 mm, 50 mm, 100 mm, or some other distance up to about 15 cm from the irradiation target 31. In one example, the first end 12a can be positioned at about 30 mm to about 100 mm, or about 25 mm to about 70 mm, or about 60 mm to about 150 mm from the irradiation target 41. Where the irradiation target is inserted within the magnetic core, it may be positioned to not be in contact with the magnetic core or any other part of the device.

In one aspect, once the irradiation target is positioned to face the first end 11a of the magnetic core 11, alternating current may be supplied to the coil 10 from a power source (not illustrated) at a predetermined frequency. For example, the frequency of the alternating current may be 50 kHz to 400 kHz. In one example, the frequency is 100 kHz. In one aspect, alternating magnetic flux parallel to the axial direction is formed on the magnetic core 11 within the coil 10. In one example, for a device 101 as illustrated in FIGS. 1(a) and 1(b), the alternating magnetic flux may be focused at the columnar portion 11b of the small cross-sectional area and emitted from the first end 11a of the magnetic core 11 to irradiate the irradiation target 31. In one aspect, the irradiation target 31 may be positioned sufficiently close to the first end 11a of the magnetic core 11 on the axis of the coil 10 to permit effective irradiation of the irradiation target 31 with the magnetic flux. In some instances, the magnetic flux density emitted from the first end 11a of the magnetic core 11 is about 0.5 mT to about 30 mT. For example, depending on the configuration of the magnetic core, the magnetic flux density emitted from the magnetic core may be about 0.5 mT to about 30 mT, or about 5 mT to about 20 mT, or about 10 mT to about 30 mT, or about 8 mT to about 25 mT. For example, the magnetic flux density may be about 10 mT, about 12 mT, about 15 mT, about 18 mT, about 20 mT, about 23 mT, about 25 mT, about 28 mT, or about 30 mT. In some instances, the magnetic flux density that irradiates the irradiation target depends on the axial position of the one end of the magnetic core relative to the one end of the coil. The magnetic flux density emitted from the magnetic core may be based on the size of the coil and the magnetic core, the configuration of the magnetic core, and/or the frequency supplied to the coil. In one example, the magnetic flux density is about 10 mT. In one aspect, magneto-sensitive heating particles may be provided to the irradiation target 31 prior to irradiation. In this aspect, the magneto-sensitive heating particles in the irradiation target 31 may be magnetically heated by the magnetic flux, and the irradiation target 31 heated by the heat generation of the magneto-sensitive heating element when exposed to the magnetic flux.

According to the example as described above, because the optical transmission path 15 is provided inside the coil 10, the thermal radiation emitted from the irradiation target 31 is transmitted through the optical transmission path 15 and can be emitted to the outside (the other side of the magnetic core). Therefore, in some examples, it is possible to visually assess light emitted (reflected) from the irradiation target 31 via the optical transmission path 15, thereby permitting accurate and easy positioning of the coil 10 with respect to the irradiation target 31.

Figure 3:
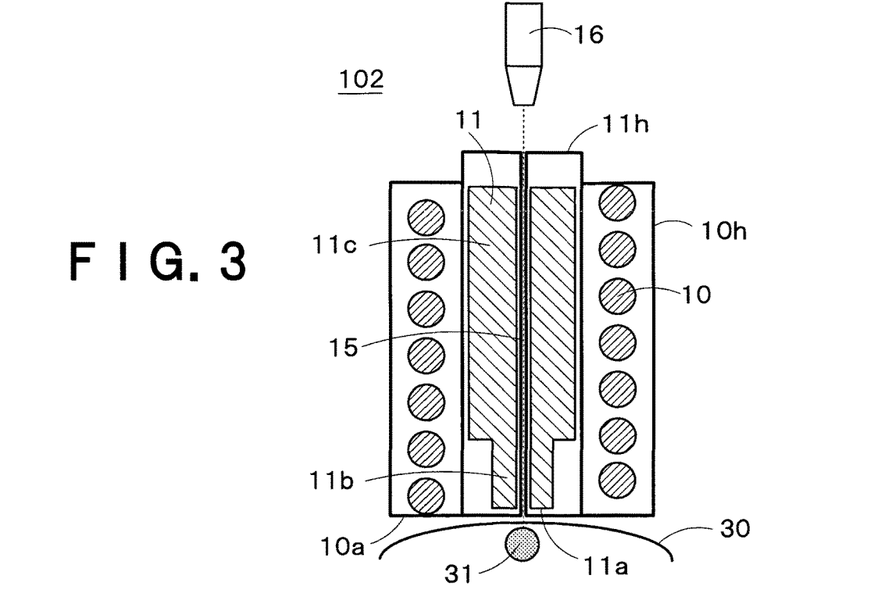
FIG. 3 is a schematic side cross-sectional view illustrating a magnetic flux irradiation device according to a second example.

A second example of a magnetic flux irradiating device is shown in FIG. 3. FIG. 3 is a schematic side cross-sectional view illustrating a magnetic flux irradiation device according to the second example.

In one aspect, as illustrated in FIG. 3, a magnetic flux irradiation device 102 may include a laser component 16 (for example, a laser pointer) on the other side of the optical transmission path 15 from the first end 11a of the magnetic core 11. In one aspect, the laser component 16 may transmit a laser beam through the optical transmission path 15 such that it emits from optical transmission path 15 at the first end 11a of the magnetic core 11. For example, if an irradiation target is positioned to face the first end 11a of the magnetic core 11, the laser beam transmitted through the optical transmission path will be incident on the irradiation target 31.

In some aspects, the other configurations for FIG. 3 are substantially the same as those of the first example illustrated in FIGS. 1(a) and 1(b). In FIG. 3, the same parts as those of the examples of FIGS. 1(a) and 1(b) are denoted by the same reference numerals, and the detailed description thereof will not be provided.

Next, the operation of magnetic flux irradiation device 102 as illustrated in FIG. 3 and described above will be described as an example of the case of irradiating the magnetic flux to the irradiation target 31 located inside the irradiation object 30 having a convex shape.

In one aspect, as illustrated in FIG. 3, the first end 11a of the magnetic core 11 is disposed to face the surface of the irradiation object 30 and the laser component 16 is activated so that a laser beam is emitted from the laser component 16. In one aspect, the emitted laser beam is transmitted through the optical transmission path 15 and is incident on the surface of the irradiation object 30.

In one aspect, the incident position of the laser beam on the surface of the irradiation object 30 is visually checked from the outside and the position of the magnetic flux irradiation device 102 and the irradiation object 30 are adjusted to align the irradiation target 31 on the axis of the coil 10. For example, the magnetic flux irradiation device 102 and the irradiation object 30 may be relatively moved, and when the incident position of the laser beam overlaps the pre-designated alignment mark, the magnetic flux irradiation device 102 and the irradiation object 30 are relatively stopped. In one aspect, the laser beam emitted from the laser component 16 permits the irradiation target 31 to be accurately positioned on the axis of the coil 10.

In another aspect, when the irradiation target 31 is positioned relative to the magnetic core 11 such that the incident position of the laser beam overlaps the alignment mark on the irradiation target 31, the first end 11a of the magnetic core 11 may be positioned to be sufficiently close to the irradiation target 31 to permit effective irradiation of the irradiation target 31. For example, the first end 11a can be positioned within about 5 mm to about 15 cm of the irradiation target 31 as discussed above. In one example, the first end 11a can be positioned about 5 mm from the irradiation target 31. In certain cases, the first 11a can be positioned within a few millimeters of the irradiation target 31 but not touching the irradiation target 31.

In this example, by the same operation as that of magnetic flux irradiation device 102, the irradiation target 31 is irradiated with the magnetic flux, and the irradiation target 31 is heated (for example, by heating of magneto-sensitive particles provided therein).

According to the above-described second example, in addition to obtaining the same advantageous effects as those in the first example, because the laser beam emitted from the laser pointer 16 is transmitted through the optical transmission path 15 and is incident on the irradiation target 31, it is possible to more accurately position the coil 10 with respect to the irradiation target 31.

Figure 4:
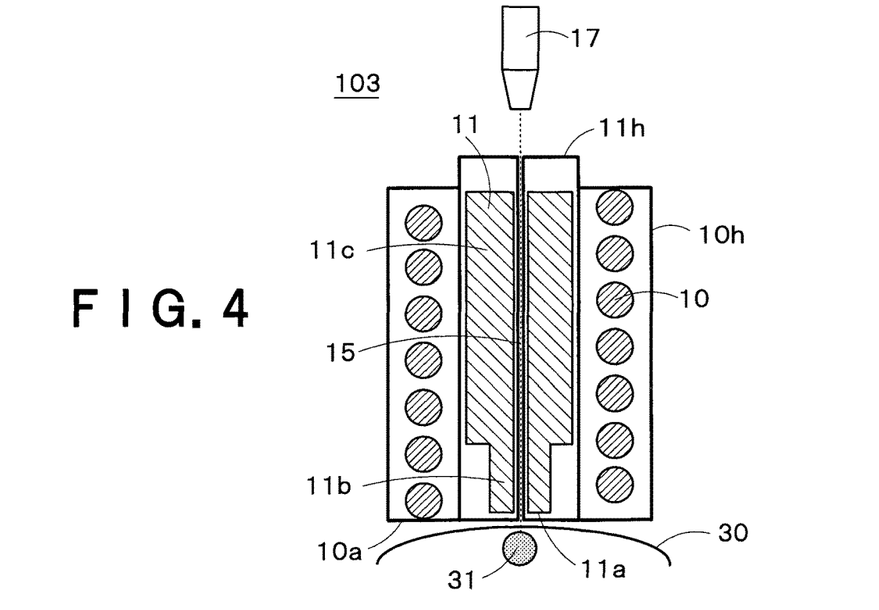
FIG. 4 is a schematic side cross-sectional view illustrating a magnetic flux irradiation device according to a third example.

A third example of a magnetic flux irradiating device is shown in FIG. 4. FIG. 4 is a schematic side cross-sectional view illustrating a magnetic flux irradiation device according to the third example.

In one example, as illustrated in FIG. 4, a magnetic flux irradiation device 103 may include a radiation thermometer 17 on the other side of the optical transmission path 15 from the first end 11a of the magnetic core 11. In one aspect, the radiation thermometer 17 may detect the thermal radiation emitted from the irradiation target 31 that is position to face the first end 11a of the magnetic core 11 and transmitted through the optical transmission path 15 from the first end 11a of the magnetic core 11 to the second end of the magnetic core. In one aspect, the radiation thermometer 17 may measure the temperature of the irradiation target 31 based on the detected results (thermal radiation).

The other configurations are substantially the same as those of the first example illustrated in FIGS. 1(a) and 1(b). In FIG. 4, the same parts of the example of FIGS. 1(a) and 1(b) are denoted by the same reference numerals, and a detailed description thereof will not be provided.

Next, the operation of this example described above will be described as an example of a case where the irradiation target 31 is located inside the irradiation object 30 having a convex shape and is irradiated with the magnetic flux.

First, by the same operation as that of the first example, after the irradiation target 31 is positioned to be sufficiently close to the one end 11a of the magnetic core 11 on the axis of the coil 10, the irradiation target 31 is irradiated with the magnetic flux, and the irradiation target 31 is heated.

In one aspect, infrared rays emitted from the irradiation target 31 may be detected in the radiation thermometer 17, and the temperature of the irradiation target 31 is measured based on the detected results. During heating of the irradiation target 31, infrared rays emitted from the irradiation target 31 may be transmitted through the optical transmission path 15 and incident on the radiation thermometer 17.

According to the above-described third example, in addition to obtaining the same advantageous effects as those of the first example, since the thermal radiation emitted from the irradiation target 31 and transmitted through the optical transmission path 15 is detected by the radiation thermometer 17, it is possible to measure the temperature of the irradiation target 31 when it is being irradiated with magnetic flux from the magnetic core 11.

A fourth example of a magnetic flux irradiation device is shown in FIGS. 5(a) and 5(b). FIG. 5(a) is a schematic side cross-sectional view illustrating the magnetic flux irradiation device according to the fourth example. FIG. 5(b) is a schematic top cross-sectional view illustrating the magnetic flux irradiation device of FIG. 5(a).

In some aspects, the cylindrical coil 10 has the properties as described above with respect to the preceding examples but the configuration of the magnetic core may vary. In one example, the magnetic core may include a plurality of columnar magnetic core elements uniformly disposed in a circumferential orientation within a cavity formed in the coil, and the optical transmission path may be configured to pass through a central region within circumferential orientation of the plurality of magnetic core elements. As illustrated in FIGS. 5(a) and 5(b), a magnetic flux irradiation device 104 according to the fourth example may have a distributed type magnetic core 12 instead of the magnetic core 11 of the magnetic flux irradiation device 101 according to the first example. In one aspect, the magnetic core may include a plurality of magnetic core elements 12e. For example, the magnetic core may include two, three, four, five or more magnetic core elements 12e. For example, the magnetic core may include four columnar magnetic core elements 12e. In this fourth example, as shown in FIGS. 5a and 5b, the magnetic core 12 may have four columnar magnetic core elements 12e that have a cylindrical shape and are uniformly disposed in the circumferential direction of the coil 10. In one aspect, the magnetic core elements 12e are radially in line with each other, for example, as shown in FIGS. 5a and 5b. In another aspect, the magnetic core elements 12e may be radially offset from each other, with some magnetic core elements 12e closer to the center of the coil than others.

In one aspect, the magnetic core elements 12e may be various different shapes. For example, the magnetic core element 12e may have a cylindrical shape or a prismatic shape. In one aspect, the dimensions of the magnetic core elements 12e may be selected based on the desired magnetic flux density or use for the device 104. In some instances, the dimensions of the magnetic core elements 12e may be selected to fit within the diameter of a central cavity defined within the coil 10 and, in particular, within a central cavity defined within the coil housing 10h, and still have sufficient room to accommodate an optical transmission path 15 formed along the axis of the coil 10 through the magnetic coil 12. In some examples, the magnetic core elements 12e may be about the same length as the coil 10 or the coil housing 10h. For example, the magnetic core elements 12e may have a diameter of about 5 mm to about 20 mm and an axial length of about 60 mm to about 240 mm. In one example, the magnetic core elements 12e may have a diameter of 10 mm and an axial length of 120 mm. In another example, the core elements 12e may have a diameter of 20 mm and an axial length of 240 mm. In another example, the core elements 12e may have a diameter of 5 mm and an axial length of 60 mm. In certain cases, the ratio of the diameter to the axial length of the core elements 12e may be about 1:2, about 1:5, about 1:8, about 1:10, about 1:12, about 1:15, or about 1:20.

In one aspect, the material of the magnetic core elements 12e comprise a magnetic material that restricts and channels magnetic eddy current fields. For example, the material of the magnetic core elements 12e can include a Mn—Zn ferrite material, a Ni—Zn material, an iron powder, a high flux powder, a permalloy powder, or an amorphous alloy. In one example, the material of the magnetic core elements 12e is a Mn—Zn ferrite material. Other magnetic materials are also contemplated for use in making the magnetic core 11.

In one aspect, the material of the magnetic core elements 12e is selected based on the desired frequency range for the device 101. For example, a Mn—Zn ferrite material may be selected for a desired frequency of 10 kHz to 2 MHz. In another example, a Ni—Zn material may be selected for a desired frequency range of 200 kHz to 100 Mhz. In another example, an iron powder may be selected for a desired frequency range of 100 kHz to 100 MHz. In another example, a high flux powder or a permalloy powder may be selected for a desired frequency range of 10 kHz to 1 Mhz. In another example, an amorphous alloy may be selected for a desired frequency range of 500 Hz to 250 kHz.

In some instances, the magnetic core elements 12e may be configured so that they are spaced apart from each other. For example, at least some of the magnetic core elements 12e may be disposed at approximately equal distances from each other. In some cases, all of the magnetic core elements 12e may be disposed at approximately equal distances from each other. In some instances, the magnetic core elements 12e may be disposed to abut against each other. In the example illustrated in FIGS. 5(a) and 5(b), the magnetic core elements 12e of magnetic flux irradiation device 104 are spaced apart from each other. When the number of the magnetic core elements increases, the magnetic core cross-sectional area increases, which may lead to distribution (decline) of the magnetic flux density emitted from the first end of the magnetic core 12a.

In one example, such as illustrated in FIG. 5(a), the coil 10 is coaxially housed within a coil housing 10h having a cavity on the inner peripheral side, and the magnetic core 12 is coaxially housed within a magnetic core housing 12h inserted into the cavity. In another aspect, the magnetic core 12 is not housed within a magnetic core housing (not shown) and is instead configured to fit within the coil 10 directly. For example, the magnetic core elements 12e may be configured in the desired orientation and affixed to each other.

In one aspect, the first end 12a of a distributed type magnetic core 12 comprises a first end of each magnetic core element 12e. As illustrated in FIG. 5(a), when the magnetic core 12 is inserted with the coil 10 to be parallel to the axis of the coil 10, the first end 12a of the magnetic core 12 may be configured to be positioned on the same plane as the first end 10a of the coil 10.

In one aspect, alternating current can be supplied to the coil 10 from a power source (not illustrated) at a predetermined frequency. For example, the alternating current can be supplied at a frequency of about 50 kHz to about 400 kHz. Alternating magnetic flux parallel to the axial direction is formed on each of the magnetic core elements 12e of the magnetic core 12 within the coil 10 when alternating current is supplied and emitted from the first end 12a of the magnetic core 12. In one aspect, the alternating magnetic flux may emit from the first end 12a of the magnetic core 12 and irradiate the irradiation target 41 disposed to face the first end 12a.

Figure 6:
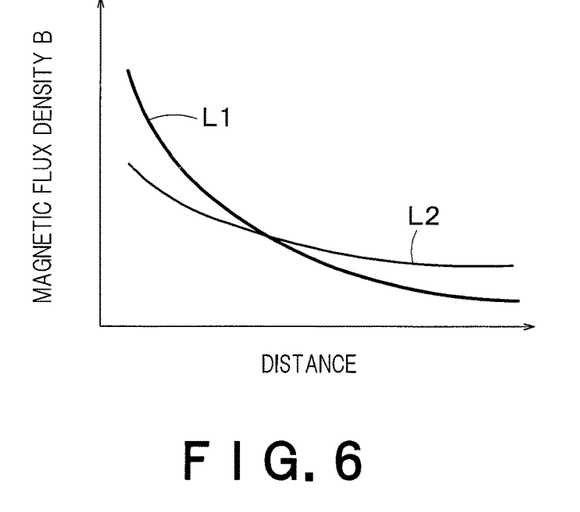
FIG. 6 is a graph illustrating a density of the magnetic flux irradiated from the magnetic core of the magnetic flux irradiation device of FIGS. 5(a) and 5(b).

FIG. 6 is a graph illustrating the magnetic flux density irradiated from the magnetic core 12 of the magnetic flux irradiation device 104 according to this example. In FIG. 6, a horizontal axis represents an axial distance starting from the one end 10a of the coil 10, and L2 represents a density of the magnetic flux irradiated from the magnetic core 12 of the magnetic flux irradiation device 104 according, to this example. L1 represents a density of the magnetic flux irradiated from the magnetic core 11 of the magnetic flux irradiation device 101 according to the first example.

In one example, as illustrated in FIG. 6, the density of the magnetic flux emitted from the magnetic core 12 of the magnetic flux irradiation device 104 according to this example is less likely to be attenuated, as compared to the density of the magnetic flux irradiated from the magnetic core 11 of the magnetic flux irradiation device 101 according to the first example (in other words, diffusion of the magnetic flux is suppressed). In one aspect, a magnetic flux irradiation device 104 having a distributed magnetic core may have reduced diffusion of magnetic flux density compared to a magnetic flux irradiation devices having a magnetic cores that is not distributed (such as described above in the first to third examples).

In one aspect, the distributed magnetic core 12 may have the optical transmission path formed in (configured to pass through) a region defined inside the magnetic core elements 12e in the radial direction of the coil 10. In another aspect, the optical transmission path may be formed on the axis of the coil 10. In one aspect, where the magnetic core 12 has a magnetic core housing 12h, an opening may be formed in the magnetic core housing 12h through which the optical transmission path 15 passes. For example, as illustrated in FIGS. 5(b) and 5(a), the optical transmission path 15 is provided in a region inside the four magnetic core elements 12e in the radial direction of the coil 10. For example, as illustrated in FIGS. 5(a) and 5(b), the optical transmission path 15 is provided to be axially transmitted through the magnetic core housing 12h on the axis of the coil 10.

Other configurations are substantially the same as those of the first example illustrated in FIGS. 1(a) and 1(b). In FIGS. 5(a) and 5(b), the same parts of the first example illustrated in FIGS. 1(a) and 1(b) are denoted by the same reference numerals, and the detailed description thereof will not be provided.

Next, the operation of this example described above will be described as an example of a case where the irradiation target 41 located at the bottom of the irradiation object 40 having a concave shape is irradiated with the magnetic flux.

In one aspect, as illustrated in FIGS. 5(a) and 5(b), the first end 12a of the magnetic core 12 can be disposed to face the surface of the irradiation object 40. In another aspect, the visible light emitted from the surface of the irradiation object 40 may be transmitted through the optical transmission path 15 and emitted to the outside from the other side of the optical transmission path 15 (the side opposite to the surface of the irradiation object 30) at the second end of the magnetic core 12. In another aspect, the surface of the irradiation object 40 may be visually checked from the other side of the the magnetic core 12 via the optical transmission path 15.

In one aspect, while the surface of the irradiation object 40 may be visually checked via the optical transmission path 15, when the magnetic flux irradiation device 102 and the irradiation object 40 may be relatively moved until it is determined by visually checking via the optical transmission path 15, that the irradiation target 41 and the magnetic flux irradiation device 102 are positioned as desired, such that the irradiation target 41 aligned with the axis of the coil 10. An alignment mark (not illustrated) may be denoted in advance at the position corresponding to the irradiation target 41 of the surface of the irradiation object 40.

Thus, in some aspects, the irradiation target 41 can be accurately positioned on the axis of the coil 10 to face the first end 12a of the magnetic core 12 using the optical transmission path 15. In one aspect, the first end 12a of the magnetic core 12 is positioned to be sufficiently close to the irradiation target 41 to permit effective irradiation of the irradiation target 41. In some instances, the coil 10 may physically interfere with the surrounding structure of the irradiation target 41 and the ability to bring the first end 12a of the magnetic core 12 close to the irradiation target 41 is impaired. In some cases, the first end 12a may be positioned to be spaced from the irradiation target 41 at a further distance from the irradiation target 41 than is sufficient for magnetic flux irradiation devices with a non-distributed core (such as those described in the first to third examples above). For example, the first end 12a can be positioned within about 5 mm to about 15 cm of the irradiation target 41. For example, the first end 12a may be positioned at a distance of about 5 mm, 10 mm, 20 mm, 30 mm, 50 mm, 100 mm, or some other distance up to about 15 cm from the irradiation target 31. In one example, the first end 12a can be positioned at about 30 mm to about 100 mm, or about 25 mm to about 70 mm, or about 60 mm to about 150 mm from the irradiation target 41. In another example, the first end 12a can be positioned no closer than about 30 mm from the irradiation target 41. In one example, the distance may be about 30 mm. In some instances, the first end 12a may be positioned about 30 mm to about 15 cm from the irradiation target 41.

In one aspect, once the irradiation target is positioned as desired to face the first end 12a of the magnetic core 12, alternating current may be supplied to the coil 10 from a power source (not illustrated) at a predetermined frequency. For example, the frequency of the alternating current may be 50 kHz to 400 kHz. In one example, the frequency is 100 kHz. In one aspect, alternating magnetic flux parallel to the axial direction is formed on each magnetic core element 12e of the magnetic core 12 within the coil 10 may irradiate to the irradiation target 41 from the one end 12a of the magnetic core 12.

In one aspect, as illustrated in FIG. 6, the density of the magnetic flux irradiated from the first end 12a of the magnetic core 12 is less likely to be attenuated (magnetic flux is less likely to be diffused). Thus, in one aspect, even if the one end 12a of the magnetic core 12 is positioned at a distance of 5 mm to 15 cm (for example, 30 mm) spaced from the irradiation target 41, the irradiation target 41 can be effectively irradiated with the magnetic flux. In some instances, the magnetic flux density emitted from the first end 12a of the magnetic core 12 is about 0.5 mT to about 30 mT as discussed above. In one example, the magnetic flux density is about 10 mT. In some instances, magneto-sensitive heating particles may be provided to the irradiation target 41 prior to irradiation. The magneto-sensitive heating particles in the irradiation target 41 may be magnetically heated by the magnetic flux, and the irradiation target 41 heated by the heat generation of the magneto-sensitive heating element when exposed to the magnetic flux.

According to the above-described fourth example, because the optical transmission path 15 is provided inside the coil 10, thermal radiation emitted from the irradiation target 41 can be transmitted through the optical transmission path 15 and can be emitted to the outside on the other side of the magnetic core 12. Therefore, in one aspect, it is possible to visually check the light emitted from the irradiation target 41 via the optical transmission path 15, thereby being able to accurately and easily position the coil 10 with respect to the irradiation target 41.

In some instances, because diffusion of the magnetic flux emitted in the axial direction from the one end 12a of the magnetic core 12 is suppressed (magnetic flux density is less likely to be attenuated), it is possible to effectively irradiate the irradiation target 41 with the magnetic flux even though the first end 12e of the magnetic core 12 cannot be brought within a very close distance to the irradiation target 41 (such as about 5 mm).

In some examples, a magnetic flux irradiation device having a distributed core (such as that illustrated in FIGS. 5a and 5b) may include a laser pointer 16 or a radiation thermometer (as discussed with respect to the second and third examples, respectively) on the other side of the optical transmission path 15 from the first end 12a of the magnetic core 12 (at the second end of the magnetic core).

In some instances, the interior of the optical transmission path 15 may be hollow. In another aspect, the interior of the optical transmission path 15 may comprise an optical transparent substance. In some cases, where a magnetic core housing 11h and 12h houses the magnetic core 11 and 12, the magnetic core housings 11h and 12h may have an opening formed therein through which the optical transmission path 15 may pass. In some instances, the magnetic core housings 11h and 12h may comprise an optical transparent substance at the position where the optical transmission path 15 is formed within the magnetic cores 11 and 12. In some examples, the magnetic core housings 11h and 12h may be made of an optical transparent substance.

Figure 7:
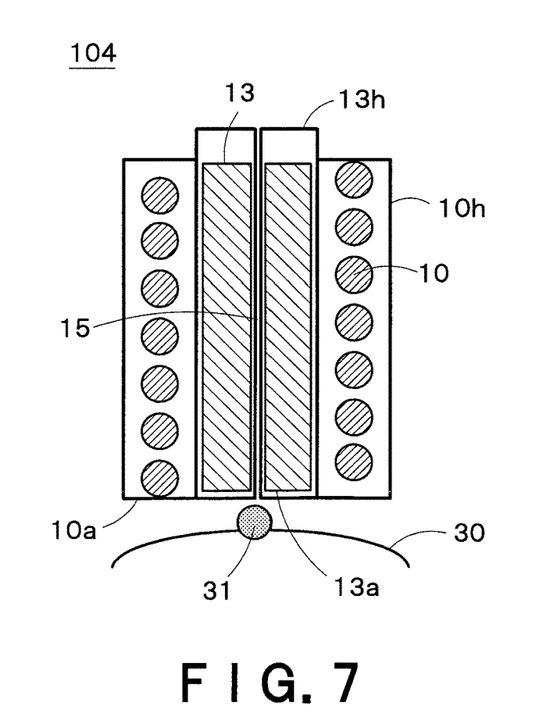
FIG. 7 is a schematic side cross-sectional view illustrating a magnetic flux irradiation device according to a fifth example.

A fifth example of the present invention will be described referring to FIG. 7. FIG. 7 is a schematic side cross-sectional view illustrating the magnetic flux irradiation device according to the fifth example. The features of the fifth example are generally the same as those set forth regarding the first to third examples except that the magnetic core 13 has a shape with a uniform cross-section.

In some aspects, the cylindrical coil 10 has the properties as described above with respect to the preceding examples but the configuration of the magnetic core may vary. In one example, a magnetic flux irradiation device 105 may have a magnetic core 13 that has a uniform cross-sectional area. The magnetic core 13 may have a cylindrical shape or a prismatic shape. The dimensions of the magnetic core 13 may be selected based on the desired frequency and use for the device 105. In one example, the diameter of the magnetic core 13 may be about 35 mm to about 140 mm. In another example, the axial length of the magnetic core 13 may be about 60 mm to about 240 mm. For example, the magnetic core 13 may have a diameter of about 35 mm and an axial length of about 60 mm. In another example, the magnetic core 13 may have a diameter of about 70 mm and an axial length of about 120 mm. In another example, the magnetic core 13 may have a diameter of about 140 mm and an axial length of about 240 mm. In some instances, the ratio of the length of the magnetic core to the diameter of the magnetic core is about 1:2 to 1:5. For example, the length of the magnetic core may be about 2 times, 3 times, 4 times, or 5 times larger than the diameter of the magnetic core. In one instance, the length of the magnetic core may be about 4 times larger than the diameter of the magnetic core. In one aspect, the optical transmission path 15 is formed continuously through the magnetic core 13 on the axis of the coil 10 from the first end 13a to the second end of the magnetic core 13. In some cases, an opening is formed in the magnetic core housing 13h at a position corresponding axially to the optical transmission path 15 at the second end of the magnetic core 13. In some instances, the magnetic core 13 is not housed in a magnetic core housing 13h.

The operation of the example device 104 as shown in FIG. 7 and described above is generally the same as described above for device 101 as shown, for example, in FIGS. 1(a) and 1(b) where the irradiation target 31 is located on the outer surface an irradiation object 30 having a convex shape, or as shown in FIG. 3 or FIG. 4 where the irradiation target 31 is located inside the irradiation object 30 having a convex shape, and is irradiated with the magnetic flux.

The devices illustrated in FIGS. 1-7 and described above are specific examples and are not limiting. For instance, while magnetic cores of specific configurations are described, other magnetic cores in which an optical transmission path is formed are contemplated.

In another aspect, the magnetic flux irradiation device may include a cylindrical coil defining a central cavity configured to receive a magnetic core parallel to an axis of the coil, the magnetic core having an optical transmission path formed therein and traversing from a first end of the magnetic core to a second end of the magnetic core, wherein the magnetic flux irradiation device is configured to irradiate magnetic flux from the first end of the magnetic core responsive to electric current supplied to the cylindrical coil, and wherein the optical transmission path is configured to transmit light incident on an irradiation target positioned to face the first end of the magnetic core, or thermal radiation emitted from the irradiation target positioned to face the first end of the magnetic core, or both. Magnetic flux irradiation devices according to these aspects are configured as described above, such as in the first to fifth examples, except that the magnetic coil is not included.

In another aspect, a magnetic core having an optical transmission path formed therein and traversing from a first end of the magnetic core to a second end of the magnetic core is provided. In one aspect, the magnetic core is configured to fit within a magnetic irradiation flux device that include a cylindrical coil defining a central cavity, the magnetic core configured to fit within the central cavity of the cylindrical coil, wherein the magnetic flux irradiation device is configured to irradiate magnetic flux from a first end of the magnetic core responsive to electric current supplied to the cylindrical coil. In one aspect, the optical transmission path in the magnetic core is configured to transmit light incident on an irradiation target positioned to face the first end of the magnetic core, or thermal radiation emitted from the irradiation target positioned to face the first end of the magnetic core, or both. Magnetic cores according to these aspects are configured as described above, such as in the first to fifth examples.

Figure 8:
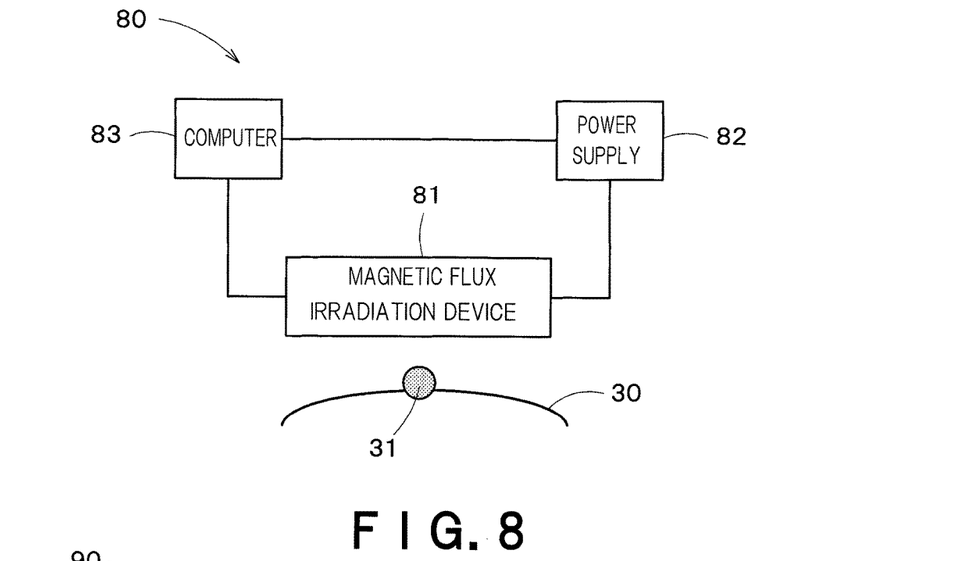
FIG. 8 is a schematic of a system including a magnetic flux irradiation device according to various examples.

FIG. 8 is a block diagram illustrating systems for using the magnetic flux irradiation devices according to certain embodiments. For example, the system 80 includes a magnetic flux irradiation device 81 having a coil 10 and a magnetic core with an optical transmission path 15 formed therein on the axis of the coil 10. The device 81 can be any of the example devices described previously in FIGS. 1 to 7 and any variations thereof as within the scope of this disclosure. The system 80 also includes a power supply 82 configured to supply electrical current to the coil 10 of the magnetic flux irradiation device 81. In some instances, the power supply 82 is configured to supply alternating current to the coil 10. The system 80 also includes a computer 83 configured to perform at least one of control operation of the magnetic flux irradiation device 81 or process data obtained from monitoring an irradiation target 31 upon which the magnetic flux irradiation device 81 is used. While irradiaton target 31 is used for illustrative purposes in FIG. 8, alternatively, irradiation target 41 or 51 may also be irradiated using system 80.

In one aspect, when the power supply 82 is activated and supplies alternating current to the coil 10, alternating magnetic flux is generated on the magnetic core. In one aspect, the alternating magnetic flux is emitted from the first end of the magnetic core and can irradiate an irradiation target 31 (such as a tumor) of an irradiation object 30 (such a subject with a tumor) that is positioned to face the first end of the magnetic core.

In one aspect, the optical transmission path 15 can be used to position the magnetic flux irradiation device 81 and the irradiation target 31 relative to each other. In some aspects, the magnetic flux irradiation device 81 further includes a laser component 16 or a radiation thermometer 17 as described herein, wherein the laser component 16 or the radiation thermometer 17 are positioned at the optical transmission path 15 at second end of the magnetic core opposite the first end of the magnetic core.

In some instances, the computer 83 may be configured to control the power supply 82. In other instances, the computer 83 may be configured to monitor the alternating current supplied to the coil 10 by the power supply 82. In some cases, the computer 83 may be configured to receive and process data about the irradiation object 30 or the irradiation target 31. For example, the computer 83 may be configured to process visual or temperature data obtained from monitoring the irradiation target 31. In another example, the computer 83 may be configured to receive optical data received through the optical transmission path 15. In another example, where the magnetic flux irradiation device 81 includes a laser component 16, the computer 83 may be configured to control operation of the laser component 16. In another example, the computer 83 may be configured to receive data about the position of the laser beam incident on the irradiation target 31 or irradiation object 30 to assist an operator in positioning the magnetic flux irradiation device 81 and the irradiation target 31 relative to each other. For example, the computer may be configured (such as by including a camera and a monitor) to assist with aligning the laser beam with the irradiation target 31 (such as on a pre-made mark on the irradiation target 31 surface). In another example, where the magnetic flux irradiation device 81 includes a radiation thermometer 17, the computer 83 may be configured to control operation of the radiation thermometer 17. For example, the computer 83 may be configured to receive data about the amount of thermal radiation emitted from the irradiation target 31 before, during, or after irradiation with the magnetic flux. In some instances, the computer 83 is configured to perform more than one of the functions described in this paragraph or one of the described functions and some other function relating to use of the device 81.

The computer 83 may be a variety of different computing devices for storing and processing data. The computer 83 may comprise, for example, a smartphone, tablet, e-reader, laptop computer, desktop computer, or a gaming device. In some embodiments, the computing device may comprise a processor interfaced with other hardware via a bus. A memory, which can include any suitable tangible (and non-transitory) computer-readable medium such as RAM, ROM, EEPROM, or the like, can embody program components that configure operation of the computer 83. The computing device may also comprise input/output interface components (for example, a display, keyboard, touch-sensitive surface, and mouse) and additional storage.

In some instances, the computer 83 may comprise a communication device. The communication device may comprise one or more of any components that facilitate a network connection. For example, the communication device may be wireless and may comprise wireless interfaces such as IEEE 802.11, Bluetooth, or radio interfaces for accessing cellular telephone networks (for example, transceiver/antenna for accessing a CDMA, GSM, UMTS, or other mobile communications network). In some cases, the communication device may be wired and may comprise interfaces such as Ethernet, USB, or IEEE 1394.

The system 80 may include additional computers each of which perform distinct functions such as those described above or other functions useful to the use of the system 80 to irradiate an irradiation target 31.

Figure 9:
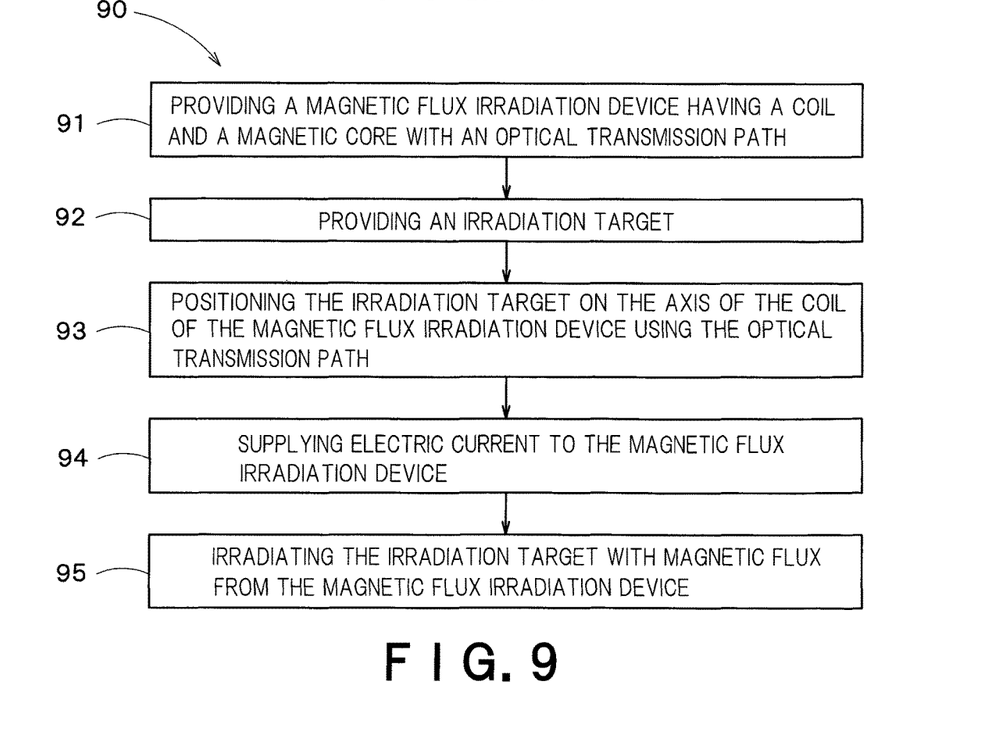
FIG. 9 is a block diagram of a method of irradiating an irradiation target of an irradiation object using a magnetic flux irradiation device according to various examples.

FIG. 9 is a block diagram illustrating methods for using the magnetic flux irradiation devices according to various embodiments. In one aspect, the method 90 is a method of irradiating an irradiation target with magnetic flux. Methods of irradiating an irradiation target with magnetic flux as described herein may be useful for treating a subject with a tumor.

In block 91, a magnetic flux irradiation device is provided. The magnetic flux irradiation device may be one of the devices specifically described in the examples provided herein or may be variations thereof as within the scope of this disclosure. In block 92, an irradiation target is provided. In one aspect, the irradiation target is on the surface of or within an irradiation object. For example, the irradiation target may be a tumor of an irradiation subject.

In block 93, the irradiation target is positioned on the axis of the coil of the magnetic flux irradiation device. In one aspect, the irradiation target is positioned to face the first end of the magnetic core of the device using the optical transmission pathway to determine the position of irradiation target. For example, a mark may be made on the surface of the target site that can be observed through the optical. transmission pathway from the second end of the magnetic core when the irradiation target is positioned facing the first end of the magnetic core and is aligned with the axis of the coil. In another aspect, the irradiation target may be positioned within a certain proximity of the first end of the magnetic core. For example, the irradiation target may be positioned about 5 mm to about 15 cm from the first end of the magnetic core.

In one aspect, the magnetic flux irradiation device selected for use in the method 90 based on the type of magnetic core it contains and the nature of the irradiation target to be irradiated. For example, the irradiation target may be on the surface of the irradiation object or just below the surface of the irradiation object, and the surface of the irradiation object may be relatively flat or may be convex. In this instance, a magnetic flux irradiation device in which the first end of the magnetic core is on the same plane as the first end of the coil may be provided (for example, as shown in FIGS. 1a and 1b). Alternatively, a magnetic flux irradiation device in which the first end of the magnetic core is recessed axially with respect to the first end of the coil may be provided (for example, as shown in FIG. 2b).

In another example, the irradiation target may be on the surface of the irradiation object or just below the surface of the irradiation object but the structure of the irradiation object may obstruct access to the irradiation target. In this instance, a magnetic flux irradiation device in which the first end of the magnetic core is protruded axially with respect to the first end of the coil may be provided (for example, as shown in FIG. 2a). In this instance, the smaller cross-section of the magnetic core as compared to the diameter of the coil permits the magnetic core to be brought within sufficient proximity to the irradiation target to be irradiated with a desired magnetic flux density. Alternatively, a magnetic flux irradiation device that includes a distributed magnetic core may be provided (for example, as shown in FIGS. 5a and 5b) and positioned at a further distance from the irradiation target. In this instance, the magnetic flux density may have reduced attenuation (dissipation) as it is emitted from the first end of the magnetic core such the irradiation target may still be irradiated with the desired magnetic flux density even though there is a greater distance between the first end of the magnetic core and the irradiation target.

In one example, when performing the method 90, a laser component 16 (such as that shown in FIG. 3) can be used to help position the irradiation target on the axis of the magnetic core (such as any of those described herein). For example, the irradiation target may be positioned using the laser component that transmits a laser beam through the optical transmission path from the second end of the magnetic core to the first end of the magnetic core to the irradiation target. In some instances, a predetermined mark can be placed on the irradiation target 31 with which the laser beam emitted by the laser component 16 may be aligned through the optical transmission path 15.

In block 94, electric current is supplied to magnetic flux irradiation device. In block 95, the irradiation target is irradiated with magnetic flux. In one aspect, the irradiation target can be irradiated with magnetic flux when electrical current is supplied to the coil (such as from a power supply) to generate magnetic flux on the magnetic core that is emitted from the first end of the magnetic core and irradiated to the irradiation target. In another aspect, the irradiation target may be positioned in sufficient proximity to the first end of the magnetic core so as to receive a desired magnetic flux density. In one aspect, the irradiation target is irradiated with a magnetic flux density of about 0.5 mT to about 30 mT as discussed above. For instance, the magnetic flux density can be about 10 mT.

In some instances, magneto-sensitive heating particles may be provided to the irradiation target prior to irradiation. In some instances, the irradiation target may contain a magneto-sensitive heating particles that heat when exposed to magnetic flux. In one aspect, the magneto-sensitive heating particles may be injected into the irradiation target. For example, the magneto-sensitive heating particles in the irradiation target may be magnetically heated by the magnetic flux, and the irradiation target heated by the heat generation of the magneto-sensitive heating element when exposed to the magnetic flux. In one example, magneto-sensitive heating particles can include magnetite particles. In another example, the magneto-sensitive heating particles may be magnetic cationic liposomes. However, a range of materials can be used to prepare magneto-sensitive heating particles and this disclosure is not limited to those described.

In one example, when performing the method 90, a radiation thermometer 17 (such as that shown in FIG. 4) can be used to measure the temperature of the irradiation target. For example, a temperature of the irradiation target surface can be monitored using the radiation thermometer before, during, or after irradiation of the irradiation target. The radiation thermometer may detect thermal radiation emitted from the irradiation target and transmitted through the optical transmission path from the first end of the magnetic core to the second end of the magnetic core to where the radiation thermometer is positioned. In some instances, the radiation thermometer can measure the irradiation target surface temperature based on detected thermal radiation.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this specification in the context of separate embodiments can also be implemented in combination in a single implementation. Conversely, various features that are described in the context of a single implementation can also be implemented in multiple ways separately or in any suitable subcombination. Moreover, although features may be described above as acting in certain combinations, one or more features from a combination can in some cases be excised from the combination, and the combination may be directed to a subcombination or variation of a subcombination. Thus, particular embodiments have been described. Other embodiments are within the scope of the disclosure.

All printed patents and publications referred to in this application are hereby incorporated herein in their entirety by this reference.

REFERENCE SIGNS LIST FOR DRAWINGS 101 magnetic flux irradiation device
102 magnetic flux irradiation device
103 magnetic flux irradiation device
104 magnetic flux irradiation device
10 coil
10a one end of coil
10h coil housing
11 magnetic core
11a one end of magnetic core 11
11b columnar portion of small cross-sectional area
11c columnar portion of large cross-sectional area
11h magnetic core housing
12 magnetic core
12a one end of magnetic core 12
12e magnetic core element
12h magnetic core housing
15 optical transmission path
16 laser pointer
17 radiation thermometer
30 irradiation object
31 irradiation target
40 irradiation object
41 irradiation target

What is claimed is:
1. A magnetic flux irradiation device comprising:
a cylindrical coil; and
a magnetic core disposed within the cylindrical coil and parallel to an axis of the coil, the magnetic core having an optical transmission path formed therein and traversing from a first end of the magnetic core to a second end of the magnetic core, a radiation thermometer positioned and configured to detect thermal radiation emitted from an irradiation target and transmitted through the optical transmission path and measure the irradiation target surface temperature based on detected thermal radiation;

wherein the magnetic flux irradiation device is configured to irradiate magnetic flux from the first end of the magnetic core responsive to electric current supplied to the cylindrical coil, and wherein the optical transmission path is configured to transmit light incident on the irradiation target, or thermal radiation emitted from the irradiation target, or both, wherein the magnetic flux irradiation device is configured to be oriented such that the first end of the magnetic core is oriented towards the irradiation target to irradiate the magnetic flux onto the irradiation target.

2. The magnetic flux irradiation device according to claim 1, wherein the magnetic core comprises a first cross-sectional columnar portion adjacent to a second cross-sectional columnar portion that defines the first end of the magnetic core, the first cross-sectional columnar portion having a greater cross-sectional area than the second cross-sectional columnar portion, and wherein the optical transmission path is configured to pass through the first cross-sectional columnar portion and the second cross-sectional columnar portion.

3. The magnetic flux irradiation device according to claim 2, wherein the first cross-sectional columnar portion and the second cross-sectional columnar portion are a single magnetic core component.

4. The magnetic flux irradiation device according to claim 2, wherein the first cross-sectional columnar portion and the second cross-sectional columnar portion are two adjoined magnetic core components.

5. The magnetic flux irradiation device according to claim 1, wherein the cylindrical coil defines an inner cavity, wherein the magnetic core comprises a plurality of columnar magnetic core elements uniformly disposed circumferentially within the inner cavity of the cylindrical coil, and wherein the optical transmission path is configured to pass through a central region within circumferential orientation of the plurality of magnetic core elements.

6. The magnetic flux irradiation device according to claim 1, further comprising a laser component positioned at the second end of the magnetic core, wherein the laser component is configured to transmit a laser beam through the optical transmission path from the second end of the magnetic core to the first end of the magnetic core.

7. The magnetic flux irradiation device according to claim 1, wherein the optical transmission path is formed parallel to the axis of the cylindrical coil.

8. The magnetic flux irradiation device according to claim 1, wherein the optical transmission path is formed at the cylindrical coil center.

9. A system comprising:
a magnetic flux irradiation device according to claim 1; and
a power supply configured to supply electrical current to the cylindrical coil of the magnetic flux irradiation device; and
a computer configured to control operation of the magnetic flux irradiation device, or process data obtained from monitoring an irradiation target upon which the magnetic flux irradiation device is used, or both.

10. The system of claim 9, wherein the power supply is configured to supply alternating current.

11. The system of claim 10, wherein the computer is configured to process visual or temperature data obtained from monitoring the irradiation target.

12. A method of irradiating an irradiation target site with magnetic flux, the method comprising:
(a) providing a magnetic flux irradiation device according to claim 1;
(b) positioning an irradiation target to face the first end of the magnetic core using the optical transmission pathway to determine the position of irradiation target; and
(c) irradiating the irradiation target with magnetic flux by supplying electrical current to the cylindrical coil to generate magnetic flux on the magnetic core that is emitted from the first end of the magnetic core to the irradiation target.

13. The method according to claim 12, wherein the irradiation target is positioned on the axis of the cylindrical coil.

14. The method according to claim 12, wherein the irradiation target is positioned using a laser component that transmits a laser beam through the optical transmission path from the second end of the magnetic core to the first end of the magnetic core to the irradiation target.

15. The method according to claim 12, wherein a temperature of the irradiation target surface is monitored using a radiation thermometer before, during, or after irradiation of the irradiation target, wherein the radiation thermometer detects thermal radiation emitted from the irradiation target and transmitted through the optical transmission path from the first end of the magnetic core to the second end of the magnetic core and measures the irradiation target surface temperature based on detected thermal radiation.

16. The method according to claim 12, wherein the irradiation target is positioned 5 mm to 15 cm from the first end of the magnetic core.

17. The method according to claim 12, wherein the magnetic flux emitted from the first end of the magnetic core has a magnetic flux density of about 0.1 mT to 30 mT.

18. The method according to claim 12, wherein the irradiation target contains magneto-sensitive heating particles that heat when exposed to magnetic flux.

19. The method according to claim 12, wherein the irradiation target is a tumor site of an irradiation subject.

* * * * *